United States Patent [19]

Rhubright et al.

[11] Patent Number: 5,817,831
[45] Date of Patent: Oct. 6, 1998

[54] ALKYLATION OF AROMATIC AMINES USING A HETERPOLY CATALYST

[75] Inventors: Douglas C. Rhubright, Chardon; James D. Burrington, Mayfield Village; Ping Y. Zhu, Willoughby Hills, all of Ohio

[73] Assignee: The Lubrizol Corporation, Wickliffe, Ohio

[21] Appl. No.: 925,109

[22] Filed: Sep. 8, 1997

Related U.S. Application Data

[63] Continuation of Ser. No. 649,372, May 17, 1996, abandoned.

[51] Int. Cl.⁶ .................................................. C07D 209/86
[52] U.S. Cl. ...................... 548/447; 544/102; 544/347; 544/35; 548/101; 548/445; 548/446; 548/447; 564/409; 502/117
[58] Field of Search ................... 564/409, 446, 564/447; 548/445, 101, 446, 447; 502/117; 544/102, 347, 35

[56] References Cited

U.S. PATENT DOCUMENTS

| | | | |
|---|---|---|---|
| Re. 34,076 | 9/1992 | Takeshita et al. | 568/790 |
| 1,662,061 | 3/1928 | Hess et al. | 260/315 |
| 3,041,349 | 11/1962 | Bearse et al. | 260/315 |
| 3,617,182 | 11/1971 | Beachem | 8/74 |
| 3,868,420 | 2/1975 | Evans et al. | 260/578 |
| 4,740,620 | 4/1988 | Dixon et al. | 564/409 |
| 5,189,201 | 2/1993 | Sano et al. | 560/205 |
| 5,214,211 | 5/1993 | Kurek et al. | 564/409 |
| 5,300,703 | 4/1994 | Knifton | 568/794 |
| 5,334,775 | 8/1994 | Gutierrez et al. | 568/791 |
| 5,503,759 | 4/1996 | Evans et al. | 252/47.5 |

FOREIGN PATENT DOCUMENTS

| | | |
|---|---|---|
| 0265932 | 5/1988 | European Pat. Off. . |
| 0226781 | 7/1988 | European Pat. Off. . |
| 4 14574 | 8/1934 | United Kingdom . |
| 421791 | 12/1934 | United Kingdom . |

OTHER PUBLICATIONS

"Selective Alkylation of Arylamines with Olefins Via Heterogeneous Acid Catalysis," paper from presentation at Solid Acid '93, 14–16 Nov. 1993.

"Heterogeneous Catalysis by Heteropoly Compounds of Molybdenum and Tungsten," Catal. Rev.—Sci. Eng., 29 23, pp. 269–321, 1987.

"Solid superacid catalysts," Chemtech, pp. 23–29, Misono et al., Nov. 1993.

"Alkylation of Benzene with Dodecene–1 Catalyzed by Supported Silicotungstic Acid," Ind. Eng. Chem. Process Res. Develop., 10, 2, 1971, Sebulsky et al.

Chem. Abst. 123:169639j (1995).

*Primary Examiner*—Brian M. Burn
*Attorney, Agent, or Firm*—David M. Shold

[57] ABSTRACT

Aliphatic hydrocarbyl-substituted aromatic amines are prepared by reacting an aromatic amine and an aliphatic hydrocarbylating agent, such as an olefin, in the presence of a heteropolyacid catalyst such as $Cs_{2.5}H_{0.5}PW_{12}O_{40}$, for a period of time and at a temperature sufficient to permit reaction.

51 Claims, No Drawings

ALKYLATION OF AROMATIC AMINES USING A HETERPOLY CATALYST

This is a continuation of application Ser. No. 08/649,372, filed May 17, 1996, now abandoned.

BACKGROUND OF THE INVENTION

The present invention relates to an improved process for preparation of alkyl-substituted aromatic amines.

U.S. Pat. No. 3,868,420, Evans et al., Feb. 25, 1975, discloses a process for the production of phenylamines alkylated in the ortho and/or para positions by alkyl groups of 1 to 4 carbon atoms and unsubstituted on the amino group, by reacting a phenylamine with an alkanol of 1 to 4 carbon atoms in the vapor phase, using a catalyst selected from aluminum oxide and aluminum oxide/molybdenum oxide mixed catalyst.

U.S. Pat. No. 5,334,775, Gutierrez et al., Aug. 2, 1994 discloses a process for alkylating hydroxyaromatic compounds with a terminally unsaturated polymer in the presence of a partially or completely dehydrated heteropoly catalyst. The polymer, as claimed, is a polymer alkylating agent of at least about 500 number average molecular weight. An example of the heteropoly catalyst is phosphotungstic acid.

U.S. Pat. No. 5,300,703, Knifton, Apr. 5, 1994 discloses synthesis of alkylphenols which comprises reacting phenol with the corresponding olefin (e.g., mixed nonenes) under adiabatic conditions in the presence of a catalyst consisting essentially of a heteropolyacid such as 12-tungstophosphoric acid, supported on an inert oxide.

U.S. Pat. No. Re. 34,076 (a reissue of U.S. Pat. No. 4,912,264), Takeshita et al., Sep. 22, 1992, discloses a process for producing hydroxy-containing alkylated aromatic compounds by liquid phase reaction of a hydroxy aromatic compound with an alkylating agent in the presence of a heteropolyacid and water. Butenes (gaseous) can be used as the alkylating agent. Among the listed catalysts are phosphotungstic acid.

SUMMARY OF THE INVENTION

The present invention provides a process for the preparation of an aliphatic hydrocarbyl-substituted aromatic amine, comprising reacting:

(a) an aromatic amine and (b) an aliphatic hydrocarbylating agent, in the presence of (c) a heteropolyacid catalyst for a period of time and at a temperature sufficient to permit reaction.

The invention further provides the product prepared thereby.

DETAILED DESCRIPTION OF THE INVENTION

The present invention provides for the preparation of aliphatic hydrocarbyl-substituted aromatic amines by the catalytic reaction of an aromatic amine with an aliphatic hydrocarbylating agent. Aromatic amines are a diverse category of compounds which are characterized by an amino group, —$NR_2$, located on an aromatic ring. The term aromatic amine, as used herein, is intended to indicate materials where the nitrogen atom in question is not a part of the aromatic structure itself; that is, the nitrogen contains predominantly $sp^3$ electron orbitals, rather than an $sp^2$ state of hybridization. That is, materials in which the nitrogen atom in question significantly participates in the aromatic character of the molecule by contributing to the aromatic $\pi$ orbitals, such as pyridine, are excluded from the present definition of aromatic amine. (However, the aromatic amines of the present invention can optionally contain pyridyl and related substituents, if an $sp^3$ nitrogen atom is also present.)

Otherwise expressed, the aromatic amines of the present invention can be described by the formula $NR^1R^2R^3$ where the Rs are hydrogen or hydrocarbyl, and at least one R is an aromatic group. Two or more of the R groups can be interconnected to form a cyclic structure. Preferably one of the Rs is hydrogen. The aromatic group will usually be a mononuclear aromatic ring (i.e., one derived from benzene) but can include fused aromatic rings, especially those derived from naphthalene, linked aromatic rings, alkyl-substituted aromatic rings, and aromatic rings containing heteroatoms such as nitrogen.

Specific examples of single ring aromatic moieties are the following:

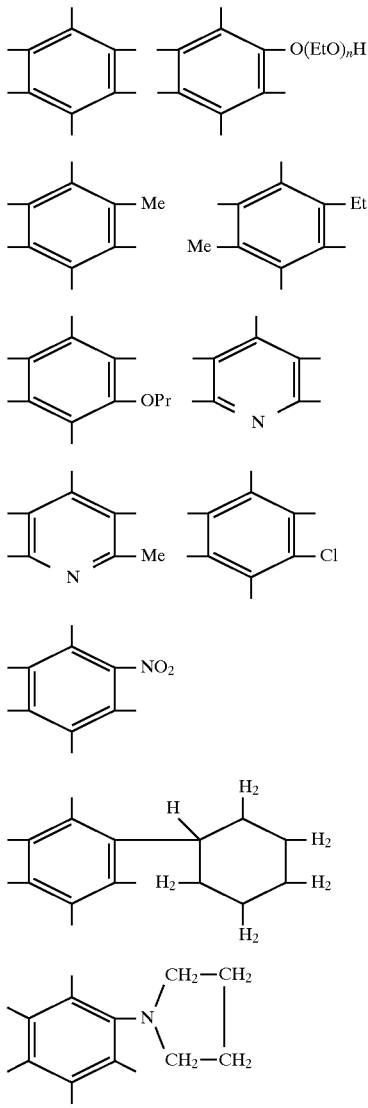

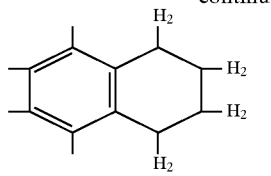

etc., wherein Me is methyl, Et is ethyl or ethylene, as appropriate, and Pr is n-propyl.

Specific examples of fused ring aromatic moieties are:

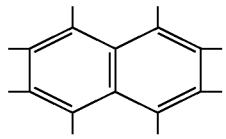

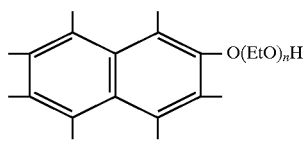

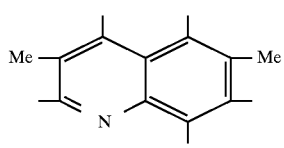

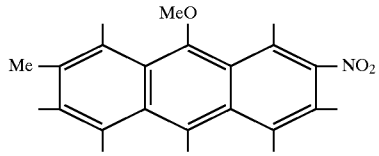

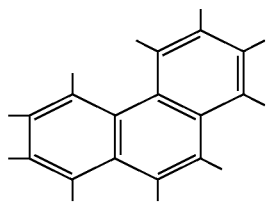

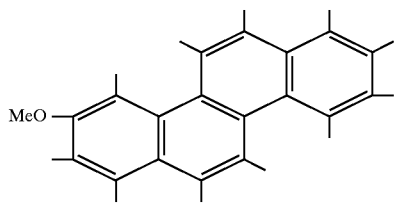

etc.

When the aromatic moiety is a linked polynuclear aromatic moiety, it can be represented by the general formula ar(—L—ar—)$_w$ wherein w is an integer of 1 to about 20, each ar is a single ring or a fused ring aromatic nucleus of 4 to about 12 carbon atoms and each L is independently selected from the group consisting of carbon-to-carbon single bonds between ar nuclei, ether linkages (e.g. —O—), keto linkages (e.g.,

sulfide linkages (e.g., —S—), polysulfide linkages of 2 to 6 sulfur atoms (e.g., —S—$_{2-6}$), sulfinyl linkages (e.g., —S(O)—), sulfonyl linkages (e.g., —S(O)$_2$—), lower alkylene linkages (e.g., —CH$_2$—, —CH$_2$—CH$_2$—, —CH$_2$—CH—)
                            |
                            R$^o$ mono(lower alkyl)-methylene linkages (e.g., —CHR$^o$—), di(lower alkyl)-methylene linkages (e.g., —CR$^o{}_2$—), lower alkylene ether linkages (e.g., —CH$_2$O—, —CH$_2$O—CH$_2$—, —CH$_2$—CH$_2$O—, —CH$_2$CH$_2$OCH$_2$CH$_2$—,

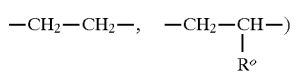

lower alkylene sulfide linkages (e.g., wherein one or more —O—'s in the lower alkylene ether linkages is replaced with a S atom), lower alkylene polysulfide linkages (e.g., wherein one or more —O— is replaced with a —S$_{2-6}$- group), amino linkages (e.g., —N—, —N—,
 |    |
 H    R$^o$ —CH$_2$N—, —CH$_2$NCH$_2$—, -alk-N—, where alk is lower alkylene, etc.), polyamino linkages (e.g., —N(alkN)$_{1-10}$ where the unsatisfied free N valences are taken up with H atoms or R$^o$ groups), linkages derived from oxo- or keto-carboxylic acids (e.g.)

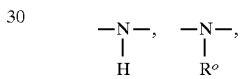

wherein each of R$^1$, R$^2$ and R$^3$ is independently hydrocarbyl, preferably alkyl or alkenyl, most preferably lower alkyl, or H, R$^6$ is H or an alkyl group and x is an integer ranging from 0 to about 8, and mixtures of such bridging linkages (each R$^o$ being a lower alkyl group).

Specific examples of linked moieties are:

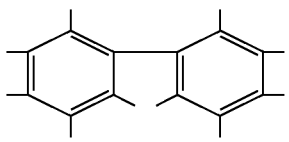

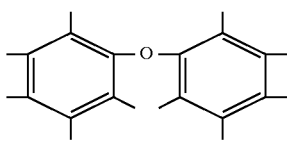

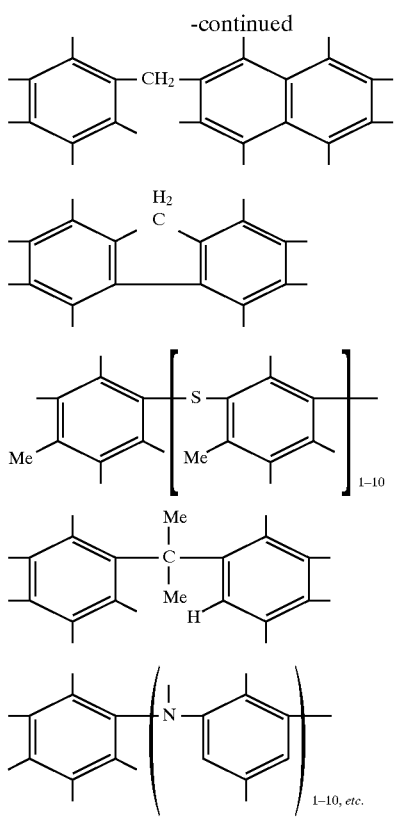

For such reasons as cost, availability, performance, etc., the aromatic group is normally a benzene nucleus, a lower alkylene bridged benzene nucleus, or a naphthalene nucleus. Most preferably the aromatic group is a benzene nucleus.

Examples of aromatic amines include aniline, di-(para-methylphenyl)-amine, naphthylamine, N,N-di(butyl)aniline, and diaromatic amines such as diphenylamine and N-methyldiphenylamine. Examples of aliphatic-substituted, cycloaliphatic-substituted, and heterocyclic-substituted aromatic monoamines are para-ethoxyaniline, para-dodecylaniline, cyclohexyl-substituted naphthylamine, and thienyl-substituted aniline.

In another embodiment, the amine can be a heterocyclic aromatic amine, in which the nitrogen atom is part of an alicyclic group. Suitable heterocyclic amines include N-phenyltetrahydropyrrole, N-phenylpiperidine, N-phenylpiperazine, and N-phenylmorpholine. Other aromatic amines are those of the general structure

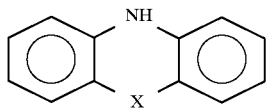

where X is SO, $SO_2$, or preferably S, O, NR, $CR_2$, or a direct bond between the aromatic rings, and R is hydrogen or a hydrocarbyl group. These materials include carbazole, phenoxazine, phenothiazine, and substituted materials of the foregoing.

For most efficient reaction, the aromatic amine preferably contains at least one aromatic ring which is free from electron-withdrawing groups, that is, groups which deactivate the ring to electrophilic aromatic substitution. Typical electron-withdrawing groups include the halogens, —$NO_2$, —$CRF_3$, —$CCl_3$, —$SO_2H$, —$SO_2R$, —$CO_2H$, —$CO_2R$, —$CONH_2$, —CHO, —CHR, and —CN.

The aromatic amine is reacted with an aliphatic hydrocarbylating agent under catalytic conditions. The term "aliphatic hydrocarbylating agent" is analogous to the conventional term "alkylating agent," except that it encompasses hydrocarbyl groups rather than merely alkyl groups, that is, materials which may have a relatively small amount of heteroatoms or substituents which do not interfere with the reaction and do not alter the substantially aliphatic hydrocarbon nature of the group, consistent with the commonly understood meaning of the term "hydrocarbyl." Thus, for example, the present reaction could be performed using as the hydrocarbylating agent the methyl ester of oleic acid, which contains an ethylenic double bond in the carbon chain, as well as ester functionality.

As used herein, the term "hydrocarbyl substituent" or "hydrocarbyl group" is thus used in its ordinary sense, which is well-known to those skilled in the art. Specifically, it refers to a group having a carbon atom directly attached to the remainder of the molecule and having predominantly hydrocarbon character. Examples of hydrocarbyl groups include:

(1) hydrocarbon substituents, that is, aliphatic (e.g., alkyl or alkenyl), alicyclic (e.g., cycloalkyl, cycloalkenyl) substituents, and aromatic-, aliphatic-, and alicyclic-substituted aromatic substituents, as well as cyclic substituents wherein the ring is completed through another portion of the molecule (e.g., two substituents together form an alicyclic radical);

(2) substituted hydrocarbon substituents, that is, substituents containing non-hydrocarbon groups which, in the context of this invention, do not alter the predominantly hydrocarbon substituent (e.g., halo (especially chloro and fluoro), hydroxy, alkoxy, mercapto, alkylmercapto, nitro, nitroso, and sulfoxy);

(3) hetero substituents, that is, substituents which, while having a predominantly hydrocarbon character, in the context of this invention, contain other than carbon in a ring or chain otherwise composed of carbon atoms. Heteroatoms include sulfur, oxygen, nitrogen, and encompass substituents as pyridyl, furyl, thienyl and imidazolyl. In general, no more than two, preferably no more than one, non-hydrocarbon substituent will be present for every ten carbon atoms in the hydrocarbyl group; typically, there will be no non-hydrocarbon substituents in the hydrocarbyl group.

The preferred aliphatic hydrocarbylating agent are in fact alkylating agents. Alkylating agents are materials which react with another material, generally an aromatic molecule, under appropriate conditions, typically acid catalyzed conditions, to provide an (or an additional) alkyl group on the aromatic molecule. Alkylating agents are well known materials and include olefins, reactive equivalents of olefins, and alkyl aromatic compounds capable of participating in a transalkylation reaction. More specifically, alkylating agents include olefins, ethers, alcohols, alkyl halide, and esters. The preferred materials are olefins, which can be straight chain or, preferably, branched. In one embodiment the olefin contains 2 to 30 carbon atoms, preferably 6 to 18, and more preferably 8 to 12 carbon atoms. Suitable olefins thus include propylene, 1- and 2- butenes, isobutene, isoprene, isoheptene, diisobutylene, mixed octenes, mixed nonenes, decenes, and dodecene, and higher olefins, particularly straight chain olefins, prepared by ethylene oligomerization or by dehydrogenation or chlorination-dehydrochlorination of straight chain paraffins. Mixtures of olefins can also be employed, including a mixture of $C_4$ olefin and olefin containing 8 to 12 carbon atoms.

Olefinic alkylating agents having at least 30 carbon atoms can also be employed. These are frequently aliphatic materials made from homo- or interpolymers (e.g., copolymers, terpolymers) of mono- and di-olefins having 2 to 10 carbon atoms, such as ethylene, propylene, butene-1, isobutene, butadiene, isoprene, 1-hexene, 1-octene, etc. Typically, these olefins are 1-mono olefins such as homopolymers of ethylene. These olefins may also be derived from halogenated (e.g., chlorinated or brominated) analogs of such homo- or interpolymers. Other sources of higher olefins include monomeric high molecular weight alkenes (e.g., 1-tetracontene) and chlorinated analogs and hydrochlorinated analogs thereof, aliphatic petroleum fractions, particularly paraffin waxes and cracked and chlorinated analogs and hydrochlorinated analogs thereof, white oils, synthetic alkenes such as those produced by the Ziegler-Natta process (e.g., poly(ethylene) greases) and other sources known to those skilled in the art. The upper chain length of such unsaturated polymeric species is not precisely defined, although materials having a molecular weight of up to 5000 are particularly useful, and especially a molecular weight of up to 2000 or 1000.

The olefin can be either a monounsaturated compound or a polyunsaturated material, i.e., a polyene. Among the suitable polyenes are dienes such as butadiene, isoprene, and the hexadienes. Other olefins include halogenated olefins such as allylic chlorides.

Other materials which are considered to be reactive equivalents of olefins include materials which may either form an olefin as an intermediate under suitable conditions, or which react under reaction conditions to form a carbonium ion equivalent to that produced by the olefin. Thus the intermediate which is believed to be prepared from the olefin

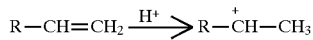

can be the same as the intermediate believed to be prepared from the corresponding alcohol:

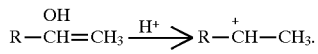

Suitable alcohols include methanol, ethanol, isopropanol, tert-butanol, sec-butanol, pentanol, hexanol, and cyclohexanol, as well as the alcohols which correspond to the higher molecular weight olefins described above. The corresponding halides, especially the alkyl chlorides and alkyl bromides, can be employed. Similarly, esters can be hydrolyzed under acid conditions to an alcohol which in turn can serve as an olefin equivalent.

Another olefin equivalent is an aliphatic-hydrocarbyl-substituted aromatic compounds, preferably an alkyl aromatic compound. Such materials are useful when the reaction is conducted under transalkylation conditions. Thus the alkyl (i.e., aliphatic hydrocarbyl) group can be transferred from one aromatic molecule to the target molecule:

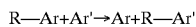

where R is an alkyl group and Ar and Ar' are aromatic groups.

For more details on alkylating agents and alkylating of aromatic materials, attention is directed to Kirk-Othmer *Encyclopedia of Chemical Technology*, 3d Ed., Vol. 2, pages 58–65 (for alkylation of aromatic hydrocarbons in general), pages 65–66 (for alkylation of phenols) and page 66 (for alkylation of aromatic amines).

Alkylation reactions are generally acid catalyzed reactions. The catalyst employed for the present alkylation reactions of the present invention is a heteropolyacid catalyst. Heteropolyacids are known materials for alkylation of hydroxyaromatic compounds. These catalysts can exist as the free acid or as a salt of a heteropolyanion. Heteropolyanions are polymeric oxoanions formed by a condensation reaction of two or more different oxoanions, e.g.,

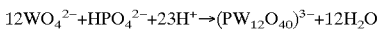

A variety of structures are known for these materials; they can have, for instance, the so-called Keggin structure, wherein twelve $WO_6$ octahedra surround a central $PO_4$ tetrahedron (in the case where phosphorus is employed). Other structures and related formulas are also known, including $PW_{12}O_{42}$, $PW_{18}O_{62}$, $P_2W_5O_{23}$, $PW_9O_{32}$, $PW_6O_{24}$, $P_2W_{18}O_{62}$, $PW_{11}O_{39}$, and $P_2W_{17}O_{61}$, where P and W are taken as representative elements and the indicated structure is an ion with the appropriate charge. The central atom of the Keggin structure, which is typically phosphorus, as shown, can also be any of the Group IIIA to Group VIIA (ACS numbering) metalloids or non-transition metals, including P, As, Si, Ge, B, Al, Sb, and Te. The tungsten (W) in the above formula fills the role known as the "poly atom," which can be any of the Group VB or VIB transition metals, including W, V, Cr, Nb, Mo, or Ta. Thus suitable materials include preferably phosphomolybdates, phosphotungstates, silicomolybdates, and silicotungstates. Other combinations selected from among the above elements are also possible, including borotungstates, titanotungstates, stannotungstates, arsenomolybdates, teluromolbydates, aluminomolybdates, and phosphovanadyltungstates, the latter representing a mixed material having a formula (for the anion portion) of $PW_{11}VO_{40}$. The preferred material is a phosphotungstate, which term generally encompasses both the acid and the various salts, described below.

The heteropoly catalysts are active both as their acid form, in which the anion is associated with the corresponding number of hydrogen ions, in the fully salt form, in which the hydrogen ions have been replaced by other cations such as metal ions, or in the partially exchanged salt form, in which a portion of the hydrogen ions have been thus replaced. Thus the catalyst can be a partially or fully exchanged alkali metal, alkaline earth metal, zirconium, chromium, manganese, iron, cobalt, nickel, copper, silver, zinc, cadmium, mercury, boron, aluminum, lead, bismuth, or ammonium or hydrocarbyl-substituted ammonium salt. Alkali metals include the metals in column 1 of the periodic table, especially lithium, sodium, potassium, rubidium, and cesium. Alkaline earth metals include metals in column 2 of the periodic table, especially magnesium, calcium, and barium. The exact stoichiometry of these materials will depend on the identity of the metals and metalloids employed in their structure. Thus a common and useful material in the acid form is $H_3PW_{12}O_{40}$. The corresponding material in the cesium salt form is $Cs_3PW_{12}O_{40}$; various partially exchanged forms, including specifically $Cs_{2.5}H_{0.5}PW_{12}O_{40}$, are also particularly useful in the present invention. In the latter material, 2.5 of the three original hydrogen ions are replaced by cesium ions. This is a relatively well defined chemical; the fractional coefficients of the Cs and the H indicate that an alternative empirical formula would be $Cs_5HP_2W_{24}O_{80}$, but the former expression is more commonly employed. The corresponding partial ammonium salt, $(NH_4)_{2.5}H_{0.5}PW_{12}O_{40}$, is also known and is effective, as is the aluminum salt, $Al_{0.83}H_{0.5}PW_{12}O_{40}$.

For more detailed information on the structures of heteropoly catalysts, attention is directed to Misono, "Heterogeneous Catalysis by Heteropoly Compounds of Molybdenum and Tungsten," *Catal. Rev.—Sci. Eng.,* 29(2&3), 269–321 (1987), in particular, pages 270–27 and 278–280.

Heteropoly acids are commercially available materials, (e.g., Aldrich Chemical Company, #22,420-0). The salts are similarly commercially available. Alternatively, they can be prepared from the acid materials by neutralization with an appropriate amount of base. For instance, the above-mentioned $Cs_{2.5}$ salt is prepared by neutralization of $H_3PW_{12}O_{40}$ with 2.5 equivalents of cesium hydroxide. The product is isolated by evaporation of the excess water.

Heteropoly acids are generally received in a hydrated form. They can be successfully employed in this form (uncalcined) or they can be treated (calcined) to remove some or all of the water of hydration, that is, to provide a dehydrated species, which sometimes exhibits improved reactivity. Calcining can be conducted by simply heating the hydrated material to a suitable temperature to drive off the desired amount of water. The heating can be under ambient pressure or reduced pressure, or it can be under a flow of air or an inert gas such as nitrogen. The calcining is preferably conducted at a temperature of at least 150° C., preferably at least 200° C., more preferably at least 250° C., for instance, at 320° C. The length of time required for the calcining is typically at least 30 minutes; preferably at least 1 hour, more preferably at least 2 hours or even 3 hours. The upper limits of temperature and time are defined largely by the economics of the process; temperatures much over 350° C. do not generally provide much advantage, nor do times in excess of about 5 hours.

The catalyst can be employed as particles of the pure acid or salt, or it can be provided on a solid support of an inert material such as alumina, silica/alumina, an aluminophosphate, a zeolite, carbon, clay, or, preferably, silica. The catalyst can be coated onto the support by well-known catalyst impregnation techniques, e.g., by applying the catalysts as a solution, followed by drying. If a support such as silica is employed, the ratio of the active catalyst component to the silica support will preferably be in the range of 0.5:99.5 to 50:50 by weight, preferably 3:97 to 40:60 by weight, and more preferably 10:90 to 30:70 by weight.

Certain supported heteropolyacid catalysts are prepared differently. Such catalysts include certain of the salts of a heteropolyacid and a metal salt or an ammonium salt, for which an insoluble heteropolyacid salt would precipitate immediately, in water, upon formation. In these cases mixtures of heteropolyacids and other metal salts (e.g., acidic metal salts) can be prepared which do not precipitate insoluble neutralization products upon mixing. The desired solid heteropolyacid salt can then be prepared by heating the intermediate material to remove water or other solvent, followed by calcination to remove volatile products of the anion. For example, mixtures of aqueous $H_3PW_{12}O_{40}$ and $Al(NO_3)_3$ or $B(OH)_3$ can be stable solutions. Such solutions, before drying and heat treatment, can be coated onto a support by conventional methods such as impregnation. After removal of water, heat treatment of the metal-heteropolyacid on the support liberates oxide(s) of nitrogen and leads to an insoluble active catalyst, uniformly coated on the support. Repeated treatment and drying cycles can be used to increase the catalyst loading.

It has been found that the activity of the catalyst is improved, and the consequent conversion of amine to alkylated amine is increased, by using catalysts having relatively greater surface areas. This can be accomplished by providing the catalyst in a supported form, wherein the underlying support material has a high surface area. It is thus preferred that the surface area of the catalyst employed should be greater than 50 $m^2/g$, preferably at least 75 $m^2/g$, and more preferably at least 100 or 200 $m^2/g$. Surface area can be measured by the BET (Braunauer, Emmett, and Teller) method, which is well-known to those skilled in the art, involving measurement of gas adsorption by the material in question. It is believed that the surface area of the supported catalyst is approximately the same as that of the underlying support.

The actual process of alkylation (or hydrocarbylation) of the aromatic amines can be either a continuous or batchwise process in which the amine, the alkylating agent (hydrocarbylating agent) and the catalyst are contacted for a suitable period of time, often at an elevated temperature. The components can be reacted neat, or an inert solvent can be employed, such as hydrocarbons such as hexane or cyclohexane, or non-aromatic oils. The reaction can be conducted under conditions such that the amine and the alkylating agent are present in the gas phase, provided that the reaction is thermodynamically or kinetically favored at the temperature and conditions employed. Specific conditions can be determined by a skilled person without undue experimentation. (In one example at 400° C. with a 2 second residence time no product was detected.) However, more commonly a liquid phase reaction is more convenient and is thus preferred.

Thus the mixture of reagents and catalyst can be contacted generally from room temperature or above, up to a temperature determined largely by the onset of decomposition of the materials or, if a liquid phase reaction is desired, the boiling point of the lowest boiling component of the mixture. Typically the temperature will be 50° to 275° C., preferably 120° to 250° C., more preferably 140° to 230° C., especially for a liquid phase reaction. Higher temperatures, e.g., 250° to 450° C., can be employed for a gas phase reaction. Elevated pressures can be employed if desired, but for ease of operation, operation at ambient pressure is employed or, alternatively, a pressure modestly in excess of ambient, e.g., sufficient to cause the reactants and products to pass through a reactor in a continuous process.

If the reaction is conducted in a batchwise manner, it can be run in a stirred reactor vessel into which the materials are charged. If the reaction is conducted continuously, it can be run in a continuous stirred tank reactor or, preferably, in a continuous plug flow process, e.g., in a tubular reactor. In a stirred reactor, the catalyst will normally reside within the reactor vessel. At the conclusion of a batchwise process, the catalyst will be removed from the products be suitable means, such as decantation, filtration, or centrifugation. In a continuous tank process, the catalyst will be retained in the reactor by other means which will be apparent to those skilled in the art of reactor design. In a continuous tubular reactor, the catalyst will normally be present in fixed bed form.

The amount of the catalyst employed will typically be 0.1 to 50 percent by weight, based on the weight of the aromatic amine reacted, and preferably 1 to 20 percent. These amounts are particularly directed to the reaction when it is conducted batchwise. When the reaction is run continuously, the amount of catalyst is better expressed in terms of liquid hourly space velocity, which is the mass of product obtained from the reactor per hour, per unit mass of catalyst employed. Continuous reactions as contemplated by the present invention typically exhibit a liquid hourly space velocity of 0.01 to 100, preferably 0.1 to 10, depending on temperature and other variables.

In the present process the catalyst can be replaced after every batch, but it is more economical to reuse the catalyst for multiple batches, or to run a continuous process for a relatively long period of time using the same catalyst. After extended use, however, the activity of the catalyst may diminish. An advantage of the present catalyst system is that the catalyst can be reactivated, or regenerated, typically by a heat treatment process such as calcining, e.g., to 450° C., preferably under a flow of air.

The particular conditions of time, temperature, pressure, and catalyst amount for a specific reaction will need to be determined according to the activity of the reactants. such adjustments can be readily made by the person skilled in the art. Thus if little or no reaction occurs at a relatively low temperature, or using a short reaction time, the conditions can be adjusted by increasing the temperature or reaction time or by adjusting the catalyst concentration.

The present reaction will lead to alkylation (or hydrocarbylation) at various sites on the amine, depending on the specific reaction conditions and the nature of the specific amine reactant and the hydrocarbylating agent. Although occasionally alkylation may occur on the nitrogen atom of the amine, more commonly it will occur predominantly an a carbon atom of the aromatic moiety. Where the aromatic moiety is a benzene ring, the product is typically alkylated on the benzene ring at a position para to the amino group, although some ortho alkylation may secondarily be observed. Para alkylation is, as a rule, favored by the use of an alkylating agent which generates a tertiary carbocation, for instance, a hindered olefin alkylating agent, rather than an alpha olefin. However, even when the alkylating agent is a commercial mixture of $C_9$ alpha olefins, by use of the present heteropolyacid catalysts, alkylation well in excess of 95% at the para position can often be attained. This is in contrast to the situations which pertains when prior art materials such as $AlCl_3$ are employed, in which case only 80 to 90% para materials are typically obtained. Depending on the reaction conditions, the product can be monoalkylated or dialkylated, or it can be a mixture of mono- and dialkylated materials.

The present invention permits alkylaromatic amines to be prepared more efficiently without the use of conventional acidic materials such as $AlCl_3$ or sulfuric acid, which cause environmental or handling difficulties, are corrosive, and are not generally reusable. The alkylaromatic amines (or aliphatic hydrocarbyl aromatic amines) prepared by the present process are useful as antioxidants, as chemical intermediates, and as additives for lubricants.

EXAMPLES

Catalyst Preparations

Example A.

A solution of cesium carbonate, $Cs_2CO_3$, 21.99 g, in 100 g of water, is added dropwise to a solution of 181.06 g $H_3PW_{12}O_{40}.nH_2O$ (85.9%, equivalent weight 2880) in 250 g water. A white precipitate forms. The resulting slurry is heated to evaporate the water, and the resulting white powder is heated in a quartz tube under air flow to 300° C. for 2 hours and 177.89 g of a white/gray powder are isolated.

Example B

A solution of 2.93 g ammonium chloride in 80 mL water is added dropwise to a solution of 74.35 g of the heteropolyacid of Example A in 250 mL water. A milky-white slurry forms. The slurry is heated to evaporate the water, and the resulting white solid is treated by heating in a glass tube under air flow to 350° C. and 65.02 g of white powder are isolated.

Example C

A solution is prepared of 29.12 g of the heteropolyacid of Example A in 50 mL of a 1:1 water/methanol mixture. A solution of aluminum nitrate nonahydrate, 2.91 g, is likewise prepared in 25 mL of 1:1 water methanol. The aluminum nitrate solution is added dropwise to the acid solution, to form a clear solution. The solution is evaporated on a hot plate to provide a yellowish solid powder. The powder is placed in a glass tube and calcined under air flow at a temperature gradually increasing to 400° C. and maintained at temperature for 1 hour. A solid, 25.39 g, is isolated.

Example D

Solutions are prepared of 12.07 g of the heteropolyacid of Example A, in 200 mL water, and of 1.11 g aluminum nitrate nonahydrate in 150 mL water. The solutions are combined and the resulting solution is used to wet 41.08 g of a silica extrudate ($SiO_2$ from PQ Corp., 1.6 mm [$\frac{1}{16}$"] extrudate). Excess solution which is not absorbed by the silica extrudate is removed, and the wetted extrudate is dried at 200° C. After drying, the treated extrudate is wetted as above with the remainder of the aqueous solution, the excess being removed as before and the extrudate dried. The silica support particles are thus treated a total of nine times, with drying after the last treatment extended to 7 hours. The resulting white particles are calcined at 450° C. under air flow, yielding 50.85 g of support and catalyst.

Example E

A suspension of 0.313 g $CaCO_3$ in 20 mL water is added to 180 mL aqueous solution of 8.47 g $H_3PW_{12}O_{40}.nH_2O$ Upon stirring, the solid $CaCO_3$ slowly disappears and the solution becomes clear. This clear solution is used to wet 28.8 g of silica microspheres (from PQ Corporation, surface area: 330 m²/g). The wetted silica microspheres are dried at 100° C. for at least 4 hours. The wetting and drying steps are repeated until all the solution is absorbed. The resulting dry white catalyst material is calcined in a flow of air at 350° C. for 2 hours, to give 33.3 g light gray catalyst.

Example F

A solution of 12.07 g of $H_3PW_{12}O_{40}.nH_2O$ in 200 mL water is combined with a solution of 1.11 g $Al(NO_3)_3.9H_2O$ in 150 mL water, to provide a clear solution. The clear solution is used to wet 41.08 g $SiO_2$ extrudate (from PQ Corporation, surface area: 200 m²/g), the silica having been first dried at 100° C. for 4 hours. The wetted silica is dried in an oven at 100°–120° C. for at least 4 hours. The wetting and drying procedures are repeated until all the solution is added and the resulting material dried. The treated extrudate is then calcined in air at 450° C. for 2 hours. The resulting catalyst composition weighs 49.5 g.

Example G

Example F is substantially repeated, employing 0.581 g of the Al salt, 5.37 g of the heteropolyacid, and 41.1 g of the silica extrudate (from PQ Corporation, surface area: 200 m²/g), in a total 150 mL water. The catalyst-coated silica is calcined at 300°–365° C. for 6 hours, yielding 44.4 g catalyst composition.

Example H

Example F is substantially repeated, employing 0.81 g of the Al salt, 8.82 g of the heteropolyacid, and 30 g of silica microspheres (PQ Corporation, surface area: 330 m²/g), in a total 260 mL water. The catalyst-coated silica is calcined at 450° C. for 2 hours, yielding 35.5 g catalyst composition.

Example J

Example F is substantially repeated, employing 1.08 g of the Al salt, 11.8 g of the heteropolyacid, and 40 g of alumina extrudate (from Engelhart, 235 m²/g), in a total 260 mL water. The catalyst-coated silica is calcined at 450° C. for 2 hours, yielding 35.5 g catalyst composition.

Example K

Example F is substantially repeated, employing 1.89 g of the Al salt, 20.6 g of the heteropolyacid, and 70 g of silica-alumina tablets (Engelhart, surface area: 310 m²/g), in a total 600 mL water. The catalyst-coated material is calcined at 450° C. for 3 hours, yielding 87.1 g catalyst composition.

Example L

Example F is substantially repeated, employing 1.35 g of the Al salt, 14.7 g of the heteropolyacid, and 50 g of silica beads (Engelhard, surface area: 700 m²/g), in a total 425 mL water. The catalyst-coated beads are calcined at 450° C. for 2 hours, yielding 61.0 g catalyst composition.

Example M

Example F is substantially repeated, employing 0.8 g of $Mg(NO_3)_2 \cdot 6H_2O$, 8.47 g of the heteropolyacid, and 28.8 g of silica microspheres (PQ Corporation, surface area: 330 m³/g), in a total 200 mL water. The catalyst-coated silica is calcined at 450° C. for 2 hours, yielding 34.2 g catalyst composition.

Alkylation Reactions.

Example 1.

A 50 mL flask, equipped with a magnetic stirrer and a nitrogen inlet, is charged with 0.14 g ($4 \times 10^{-5}$ moles) of $Cs_{2.5}H_{0.5}PW_{12}O_{40}$ (which has been calcined at 320° C. under an air flow for 3 hours) and 1.18 g (0.007 moles) diphenylamine. The mixture is heated with stirring to 140° C. and maintained at temperature for 15 minutes. A commercial mixture of predominantly $C_9$ olefins, 2.30 g (0.018 moles) is added dropwise over 10 minutes. The reaction mixture is maintained at 145° C. for 24 hours.

Upon cooling to 40° C., the reaction mixture is diluted with 20 mL cyclohexane, and the mixture is subjected to centrifugation to separate the solids. The liquid phase is washed consecutively with water, aqueous sodium bicarbonate, and water. The resulting organic phase is stripped under house vacuum at 200° C. to yield 2.16 g alkylated amine.

Example 2.

A stirred vessel is charged with 0.33 g of the $Cs_{2.5}$ catalyst of example 1 and 1.20 g of diphenylamine. The mixture is mixed and heated to 135° C., whereupon 1.33 g of the commercial $C_9$ alkyl olefins of example 1 are added, dropwise. The mixture is heated to 150° C. and maintained at temperature for 8 hours. An additional 1.08 g of the alkylolefins is added dropwise and the reaction continued for a total of 48 hours. An additional 0.32 g of the catalyst is added and the reaction is maintained at 150° C. for an additional 20 hours. The reaction product is worked up substantially as in example 1.

Example 3.

Example 1 is substantially repeated except that in place of the diphenyl amine there is used a corresponding amount of carbazole. The mole ratio of carbazole to olefin is 1:3; the reaction temperature is 150° C. A negligible amount of the alkylated product is obtained, due, it is believed, to minimal solubility of carbazole under the reaction conditions and the formation of a multiphase system; reaction at higher temperature will provide alkylated product.

Example 4.

Example 1 is substantially repeated except that carbazole is used in place of the diphenyl amine and hexadecene is used in place of the $C_9$ olefin mixture. The mole ratio of amine:olefin is 1:2.7. The amount of catalyst is 6% by weight based on the total organic materials charged. The reaction temperature is 250° C., at which temperature the carbazole melts or is soluble; the reaction time is 8 hours. Alkylated carbazole is obtained.

Example 5.

A Parr bomb, equipped with thermocouple, mechanical stirrer, and venting valves, is charged with 1.30 g $H_3PW_{12}O_{40}$ (calcined at 300° C.), 28.55 g commercial $C_9$ olefins, 15.31 g diphenylamine, and 17 g cyclohexane. The bomb is sealed and heated to 250° C. and maintained at temperature for about 8 hours. The mixture is cooled and analyzed by infrared spectroscopy to show the formation of alkylated material.

(A few similar examples employing a reaction temperature of 125° or 150° C. at ambient pressure produce little or no product, although this is not believed to represent a general limitation.)

Example 6.

A Paar bomb equipped with thermocouple and mechanical stirrer is charged with 0.70 g of the $Cs_{2.5}$ catalyst of example 1, 13.87 g of diphenylamine, and 25.85 g commercial C9 olefins. the bomb is sealed and heated to 250° C. over 1.25 hours, at which point the pressure reaches 1.2 MPa (180 psi). The mixture is heated at 250° C. for a total of 7.5 hours. The mixture is cooled and analyzed by infrared spectroscopy to show the formation of alkylated material.

Example 7

A stainless steel tube, 19 mm (¾ inch) inside diameter, is loaded with 100 g of a catalyst of $H_3PW_{12}O_{40}$ loaded at a 10% loading on a silica (from PQ Corp., having a surface area of 200 m²/g). The tube, containing the catalyst, is heated to 154° C. (310° F.) in a tube furnace. A feed mixture of C-9 olefins, diphenylamine, and cyclohexane, in a weight ratio of 45:25:30, is introduced to the bottom of the reactor at a flow rate of 0.27 g/min. The effluent is collected and the cyclohexane is stripped under vacuum. The product is the alkylated material.

Example 8

A 3-neck 250 mL flask is fitted with a magnetic stirring bar, a condenser, a temperature controller, and an addition funnel, under a flow of nitrogen. To the flask is added 25.4 g diphenylamine (0.15 mol) and 12.7 g $Cs_{2.5}H_{0.5}PW_{12}O_{40}$ (50 weight percent based on diphenylamine) and the materials are mixed and heated to 150° C. Thereafter 51.1 g commercial nonenes (0.405 mol, 2.7 molar equivalent based on diphenylamine) are added dropwise from the addition funnel over a period of about 20 minutes. The resulting mixture is refluxed under nitrogen for 72 hours before cooling to room temperature. The reaction mixture is centrifuged, and the clear upper solution is decanted, filtered through filter aid, and stripped under house vacuum at 130° C. to yield 38 g of alkylated amine. The remaining solid is the recovered catalyst. Analytical results by $^1H$—NMR are listed in Table I. (DPA is diphenylamine.)

Example 9

The crude recovered catalyst from example 8 is mixed with fresh diphenylamine (25.4 g) and reacted with nonenes (51.1 g) in a similar way as in example 8. Alkylated amine, 46 g is obtained after refluxing for 72 hours. Analytical results by $^1H$—NMR are listed in Table I.

Example 10

In a similar manner as in example 8, 25.4 g of diphenylamine and 12.7 g of $Cs_{2.5}H_{0.5}PW_{12}O_{40}$ are mixed and heated to 250° C. Thereafter 51.1 g of commercial nonenes are added over 7 hours during which time the temperature drops slowly to 154° C. The mixture is heated at 154° C. for 90 minutes before cooling to room temperature. The product is worked up as in example 8 to afford 39 g of alkylated amine. Analytical results by $^1H$—NMR are listed in Table I.

Example 11

In a similar manner as in example 8, 25.4 g of diphenylamine and 51.1 g of commercial nonenes are refluxed in the presence of 12.7 g of $Cs_{2.5}H_{0.5}PMo_{12}O_{40}$ for 24 hours to yield a semi-solid material which is analyzed by infrared spectroscopy to show the formation of alkylated amine.

Example 12

In a similar manner as in example 8, 25.4 g of diphenylamine and 51.1 g of commercial nonenes are refluxed in the presence of 14 g of $(NH_4)_{2.5}H_{0.5}PW_{12}O_{40}$ for 26 hours. The product is worked up as example 9 to afford 40 g of alkylated amine. Analytical results by $^1H$—NMR are listed in Table I.

Example 13

In a similar manner as in example 8, 17.6 g of diphenylamine (0.104 mol) and 35.4 g of commercial nonenes (0.281 mol) are refluxed in the presence of 4.4 g of $Al_{0.83}H_{0.5}PW_{12}O_{40}$ (25 weight percent based on diphenylamine) for 15 hours to yield a semi-solid material which is analyzed by infrared spectroscopy to show the formation of alkylated amine.

Example 14

In a similar manner as in example 8, 16.6 g of diphenylamine (0.0981 mol) and 33.4 g of commercial nonenes (0.265 mol) are refluxed in the presence of 8.3 g of $Al_{0.83}H_{0.5}PW_{12}O_{40}$ (20 weight percent catalyst, supported on a commercial silica extrudate) for 30 hours. Alkylated material, 37 g, is isolated by decanting to remove the recovered solid catalyst and subsequent product workup. Analytical results by $^1H$—NMR are listed in Table I.

Example 15

The recovered solid $Al_{0.83}H_{0.5}PW_{12}O_{40}$ from example 14 is mixed, without purification, with 16.6 g of fresh diphenylamine and refluxed with 33.4 g of commercial nonenes for 24 hours. Alkylated material, 40 g, is isolated from the solid catalyst by decanting and subsequent workup, and the catalyst is saved for use in example 16. Analytical results by $^1H$—NMR are listed in Table I.

Example 16

The recovered $Al_{0.83}H_{0.5}PW_{12}O_{40}$ on silica catalyst from example 15 is used again with 16.6 g of fresh diphenylamine and 33.4 g of commercial nonenes. After refluxing for 30 hours, 45 g of alkylated material is isolated from the solid catalyst by decanting and subsequent workup. Analytical results by $^1H$—NMR are listed in Table I.

Example 17

In a similar manner as in example 8, 25.4 g of diphenylamine and 51.1 g of commercial nonenes are refluxed in the presence of 12.7 g of $Al_{0.83}H_{0.5}PW_{12}O_{40}$ (20 weight percent catalyst supported on a commercial silica microspheres) for 30 hours. Alkylated material, 45.9 g, is isolated by centrifuging and decanting to remove the spent solid catalyst, with subsequent workup. Analytical results by $^1H$—NMR are listed in Table I.

Example 18

Example 14 is repeated with a larger scale. Thus, 50.8 g of diphenylamine (0.300 mol) and 102.3 g of commercial nonenes (0.811 mol) are refluxed in the presence of 25.4 g of $Al_{0.83}H_{0.5}PW_{12}O_{40}$ (20 weight percent catalyst supported on a commercial silica extrudate) for 34.5 hours. The resulting material is centrifuged, and the clear upper solution is filtered through a pad of filter aid and stripped under house vacuum at 160° C. to yield 90.5 g of alkylated amine. Analytical results by $^1H$—NMR are listed in Table I.

Example 19

In a similar manner as in example 8, 25.4 g of diphenylamine and 51.1 g of commercial nonenes are refluxed in the presence of 12.7 g of $Al_{0.83}H_{0.5}PW_{12}O_{40}$ (20 weight percent supported on a commercial alumina extrudate) for 30 hours. 61.5 g of alkylated material is isolated by centrifuging and decanting to remove the spent solid catalyst. Analytical results by $^1H$—NMR are listed in Table I.

Example 20

In a similar manner as in example 8, 25.4 g of diphenylamine and 51.1 g of commercial nonenes are refluxed in the presence of 12.7 g of $Al_{0.83}H_{0.5}PW_{12}O_{40}$ (20 weight percent supported on a commercial silica-alumina tablet) for 29 hours. 69.2 g of alkylated material is isolated by centrifuging and decanting to remove the spent solid catalyst. Analytical results by $^1H$—NMR are listed in Table I.

Example 21

In a similar manner as in example 8, 25.4 g of diphenylamine and 51.1 g of commercial nonenes are refluxed in the presence of 12.7 g of $Al_{0.83}H_{0.5}PW_{12}O_{40}$ (10 weight percent supported on a commercial active carbon, Darco™ 4–12 mesh) for 29 hours. 58.0 g of alkylated material is isolated by centrifuging and decanting to remove the spent solid catalyst. Analytical results by $^1H$—NMR are listed in Table I.

Example 22

In a similar manner as in example 8, 25.4 g of diphenylamine and 51.1 g of commercial nonenes are refluxed in the presence of 12.7 g of $Al_{0.98}H_{0.07}PW_{12}O_{40}$ (10 weight percent supported on a commercial silica extrudate) for 42.5 hours. 44.0 g of alkylated material is isolated by centrifuging and decanting to remove the spent solid catalyst. Analytical results by $^1H$—NMR are listed in Table I.

Example 23

In a similar manner as in example 8, 25.4 g of diphenylamine and 51.1 g of commercial nonenes are refluxed in the presence of 12.7 g of $Ca_{1.25}H_{0.5}PW_{12}O_{40}$ (20 weight percent supported on a commercial silica microspheres) for 30 hours. 47.5 g of alkylated material is isolated by centrifuging and decanting to remove the spent solid catalyst. Analytical results by $^1H$—NMR are listed in Table I.

TABLE I

| Example | unreacted DPA, % | mono-alkylated DPA, % | di-alkylated DPA, % | para-alkylated DPA, % |
| --- | --- | --- | --- | --- |
| 8 | 14 | 48 | 38 | >>95 |
| 9 | 16 | 58 | 26 | >>95 |
| 10 | 31 | 56 | 13 | >>95 |
| 12 | 14 | 69 | 17 | >>95 |
| 14 | 7 | 40 | 53 | >95 |
| 15 | 9 | 46 | 45 | >95 |
| 16 | 14 | 59 | 36 | >95 |
| 17 | 8 | 38 | 54 | >95 |
| 18 | 7 | 42 | 51 | >95 |
| 19 | 20 | 54 | 26 | >95 |
| 20 | 8 | 44 | 48 | >95 |
| 21 | 24 | 57 | 19 | >95 |
| 22 | 7 | 39 | 54 | >95 |
| 23 | 4 | 43 | 53 | >95 |

Each of the documents referred to above is incorporated herein by reference. Except in the Examples, or where otherwise explicitly indicated, all numerical quantities in this description specifying amounts of materials, reaction conditions, molecular weights, number of carbon atoms, and the like, are to be understood as modified by the word "about." Unless otherwise indicated, each chemical or composition referred to herein should be interpreted as being a commercial grade material which may contain the isomers, by-products, derivatives, and other such materials which are normally understood to be present in the commercial grade. However, the amount of each chemical component is presented exclusive of any solvent or diluent oil which may be customarily present in the commercial material, unless otherwise indicated. As used herein, the expression "consisting essentially of" permits the inclusion of substances which do not materially affect the basic and novel characteristics of the composition under consideration.

What is claimed is:

1. A process for the preparation of an aliphatic hydrocarbyl-substituted aromatic amine, comprising reacting:

(a) an aromatic amine and
(b) an aliphatic hydrocarbylating agent, in the presence of
(c) a heteropolyacid catalyst for a period of time and at a temperature sufficient to permit reaction.

2. The process of claim 1 wherein the aromatic amine contains at least one aromatic ring which is free from electron-withdrawing groups.

3. The process of claim 1 wherein the aromatic amine is a diaromatic amine.

4. The process of claim 1 wherein the aromatic amine is diphenylamine.

5. The process of claim 1 where the amine has the structure

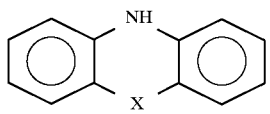

where X is S, O, NR, SO, $SO_2$, $CR_2$, or a direct bond between the aromatic rings, and R is hydrogen or a hydrocarbyl group.

6. The process of claim 1 wherein the amine is carbazole.

7. The process of claim 1 wherein the hydrocarbylating agent is an olefin, a reactive equivalent of an olefin, or an alkyl aromatic compound capable of participating in a transalkylation reaction.

8. The process of claim 1 wherein the aliphatic hydrocarbyl group is an alkyl group and the aliphatic hydrocarbylating agent is an alkylating agent.

9. The process of claim 8 wherein the alkylating agent is an olefin.

10. The process of claim 9 wherein the olefin is a branched olefin.

11. The process of claim 9 wherein the olefin comprises a polymeric species having olefinic unsaturation and having a molecular weight of up to about 5000.

12. The process of claim 9 wherein the olefin contains 2 to about 30 carbon atoms.

13. The process of claim 9 wherein the olefin contains about 6 to about 18 carbon atoms.

14. The process of claim 9 wherein the olefin contains about 8 to about 12 carbon atoms.

15. The process of claim 9 wherein the olefin comprises a mixture of $C_4$ olefin and olefin containing about 8 to about 12 carbon atoms.

16. The process of claim 9 wherein the olefin comprises a $C_9$ olefin mixture.

17. The process of claim 8 wherein the alkylating agent is an ether, alcohol, alkyl halide, or ester, and the reaction is conducted under conditions in which such component functions as a reactive equivalent of an olefin.

18. The process of claim 8 wherein the alkylating agent is an alkyl aromatic compound and the reaction is conducted under transalkylation conditions.

19. The process of claim 18 wherein the alkyl aromatic compound is an alkyl phenol.

20. The process of claim 1 wherein the heteropolyacid catalyst is a phosphomolybdate, a phosphotungstate, a silicomolybdate, or a silicotungstate.

21. The process of claim 20 wherein the heteropolyacid catalyst is a phosphotungstate.

22. The process of claim 1 wherein the heteropolyacid catalyst is a partially or fully exchanged alkali metal, alkaline earth metal, zirconium, chromium, manganese, iron, cobalt, nickel, copper, silver, zinc, cadmium, mercury, boron, aluminum, lead, bismuth, or ammonium salt.

23. The process of claim 22 wherein the heteropolyacid catalyst is a partially exchanged cesium salt.

24. The process of claim 23 wherein the heteropolyacid catalyst contains on the average about 2.5 cesium ions and about 0.5 hydrogen ions per structural unit.

25. The process of claim 24 wherein the heteropolyacid catalyst is represented by the formula $Cs_{2.5}H_{0.5}PW_{12}O_{40}$.

26. The process of claim 22 wherein the heteropolyacid catalyst is a partially exchanged ammonium salt.

27. The process of claim 26 wherein the heteropolyacid catalyst is represented by the structure $(NH_4)_{2.5}H_{0.5}PW_{12}O_{40}$.

28. The process of claim 1 wherein the heteropolyacid catalyst is hydrated or dehydrated.

29. The process of claim 1 wherein the heteropolyacid catalyst has been calcined prior to use.

30. The process of claim 29 wherein the calcining is conducted at at least about 150° C.

31. The process of claim 29 wherein the calcining is conducted at at least about 200° C.

32. The process of claim 29 wherein the calcining is conducted at at least about 250° C.

33. The process of claim 1 wherein the reaction is conducted at about 50° to about 450° C.

34. The process of claim 1 wherein the reaction is conducted in the liquid phase at about 50° to about 275° C.

35. The process of claim 34 wherein the reaction is conducted at about 140° to about 230° C.

36. The process of claim 1 wherein the reaction is conducted in the gas phase at about 250° to about 450° C.

37. The process of claim 1 wherein the heteropolyacid catalyst is provided on a solid support.

38. The process of claim 37 wherein the surface area of the catalyst is greater than about 50 $m^2/g$.

39. The process of claim 37 wherein the surface area of the catalyst is at least about 75 $m^2/g$.

40. The process of claim 37 wherein the surface area of the catalyst is at least about 100 $m^2/g$.

41. The process of claim 37 wherein the solid support is silica, alumina, silica/alumina, an aluminophosphate, a zeolite, carbon, or clay.

42. The process of claim 38 wherein the support is silica.

43. The process of claim 39 wherein the ratio of heteropolyacid catalyst to silica is about 0.5:99.5 to about 50:50 by weight.

44. The process of claim 39 wherein the ratio of heteropolyacid catalyst to silica is about 3:97 to about 40:60 by weight.

45. The process of claim 1 wherein the process is a continuous process.

46. The process of claim 45 wherein the process is a continuous plug flow process.

47. The process of claim 45 wherein the process is conducted in a tubular reactor.

48. The process of claim 45 wherein the reaction is conducted at about 145° to about 160° C. at near ambient pressure.

49. The process of claim 45 wherein the process has a linear hourly space velocity of 0.01 to 100.

50. The process of claim 45 wherein the linear hourly space velocity is 0.1 to 10.

51. The process of claim 1 wherein the amount of the heteropolyacid catalyst is about 0.1 to about 50 percent by weight of the aromatic amine reacted.

* * * * *